US009700199B2

(12) United States Patent
Tomatsu et al.

(10) Patent No.: US 9,700,199 B2
(45) Date of Patent: Jul. 11, 2017

(54) IMAGE PROCESSING APPARATUS AND IMAGE PROCESSING METHOD

(71) Applicant: CANON KABUSHIKI KAISHA, Tokyo (JP)

(72) Inventors: Nobuhiro Tomatsu, Yokohama (JP); Makoto Sato, Tokyo (JP); Tomoyuki Makihira, Tokyo (JP); Yoshihiko Iwase, Yokohama (JP); Kazuhide Miyata, Yokohama (JP); Hiroyuki Shinbata, Tama (JP); Ritsuya Tomita, Yokohama (JP); Daisuke Kibe, Kawaguchi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/909,072

(22) PCT Filed: Jul. 24, 2014

(86) PCT No.: PCT/JP2014/070148
§ 371 (c)(1),
(2) Date: Jan. 29, 2016

(87) PCT Pub. No.: WO2015/016292
PCT Pub. Date: Feb. 5, 2015

(65) Prior Publication Data
US 2016/0157710 A1   Jun. 9, 2016

(30) Foreign Application Priority Data

Jul. 31, 2013  (JP) .................................. 2013-159175

(51) Int. Cl.
*A61B 3/14*   (2006.01)
*A61B 3/10*   (2006.01)
(Continued)

(52) U.S. Cl.
CPC .......... *A61B 3/0025* (2013.01); *A61B 3/0041* (2013.01); *A61B 3/102* (2013.01);
(Continued)

(58) Field of Classification Search
USPC ................................................ 351/200–246
See application file for complete search history.

(56) References Cited

U.S. PATENT DOCUMENTS

2003/0048540 A1*  3/2003  Xie ........................ A61B 3/102
                                                            359/637
2010/0110172 A1   5/2010  Satake
(Continued)

FOREIGN PATENT DOCUMENTS

| JP | 2007-130403 A | 5/2007 |
| WO | 2009/141769 A1 | 11/2009 |
| WO | 2010/122118 A1 | 10/2010 |

OTHER PUBLICATIONS

Erich Gotzinger, High Speed Spectral Domain Polarization Sensitive Optical Coherence Tomography of the Human Retina, Optics Express 10217, Dec. 12, 2005, vol. 13, No. 25.

*Primary Examiner* — Mohammed Hasan
(74) *Attorney, Agent, or Firm* — Canon USA Inc., IP Division

(57) ABSTRACT

To accurately position multiple tomographic image.
An image processing apparatus includes a detecting unit configured to detect motion of an eye in a plurality of polarization-sensitive tomographic images, based on a predetermined region extracted from the plurality of polarization-sensitive tomographic images of the eye, and a positioning unit configured to position a plurality of tomographic luminance images corresponding to the plurality of polarization-sensitive tomographic images, based on the detected movement.

19 Claims, 6 Drawing Sheets

(51) Int. Cl.
 *A61B 3/00* (2006.01)
 *A61B 3/113* (2006.01)
 *G06T 7/33* (2017.01)
 *G06T 7/246* (2017.01)

(52) U.S. Cl.
 CPC ............ *A61B 3/113* (2013.01); *A61B 3/14* (2013.01); *G06T 7/248* (2017.01); *G06T 7/337* (2017.01); *G06T 2207/10101* (2013.01); *G06T 2207/30041* (2013.01)

(56) References Cited

U.S. PATENT DOCUMENTS

| | | | |
|---|---|---|---|
| 2011/0267340 A1 | 11/2011 | Kraus | |
| 2011/0267580 A1* | 11/2011 | Nakajima | G06K 9/00597 351/206 |
| 2012/0249962 A1 | 10/2012 | Uchida | |
| 2012/0321166 A1* | 12/2012 | Kitamura | A61B 3/0058 382/131 |
| 2013/0188134 A1 | 7/2013 | Iwase | |

* cited by examiner

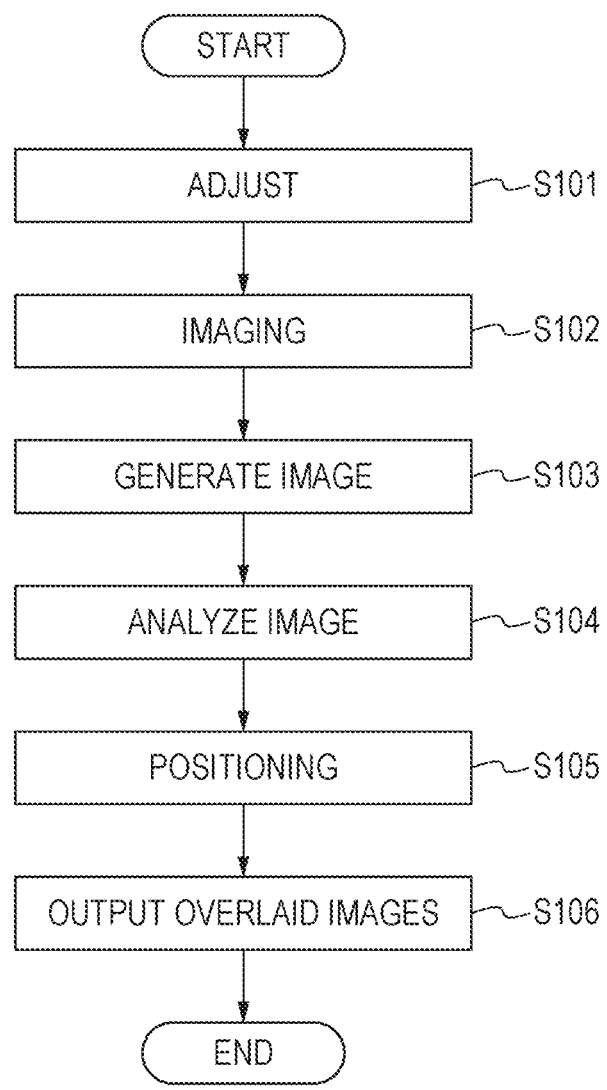

IMAGE PROCESSING APPARATUS AND IMAGE PROCESSING METHOD

TECHNICAL FIELD

The present invention relates to an image processing apparatus and image processing method.

BACKGROUND ART

Optical coherence tomography (OCT) using multi-wavelength light-wave interference can obtain tomographic images of specimens (particularly the fundus) at high resolution.

In recent years, ophthalmologic OCT apparatuses have come to acquire polarization sensitive OCT images using polarization parameters (retardation and orientation) which are a type of optical properties of fundus tissue, in addition to normal OCT images where the shape of the fundus tissue is imaged.

A polarization sensitive OCT image can be configured and fundus tissue can be distinguished and segmented using polarization parameters in polarization sensitive OCT. PTL 1 discloses that in polarization sensitive OCT, light which has been modulated into circularly-polarized light is used as measurement light to observe a specimen, and interference light is split as two orthogonal linearly-polarized lights and detected, thereby generating a polarization sensitive OCT image.

Also, in diagnosis using an ophthalmologic OCT apparatus, there may be distortion in the image due to motion of the eye while imaging, preventing improvement in accuracy of diagnosis and treatment. It should be understood that even when an eye is fixed on one point, small vibrations are unwittingly being repeated (involuntary eye movement). Accordingly, measures need to be taken to eliminate the influence of involuntary eye movement from acquired images when performing diagnosis or treatment of the eye. PTL 2 discloses positioning of multiple tomographic images making up a three-dimensional image of the fundus.

CITATION LIST

Patent Literature

PTL 1 International Publication No. WO 2010/122118A1
PTL 2 Japanese Patent Laid-Open No. 2007-130403

Non Patent Literature

NPL 1 E. Gotzinger et al., Opt. Express 13, 10217, 2005

SUMMARY OF INVENTION

Solution to Problem

An image processing apparatus according to the present invention includes: a tomographic image acquiring unit configured to acquire a plurality of polarization-sensitive tomographic images of an eye; an extracting unit configured to extract a predetermined region from the plurality of polarization-sensitive tomographic images; a detecting unit configured to detect motion of the eye in the plurality of polarization-sensitive tomographic images, based on the extracted predetermined region; and a positioning unit configured to position a plurality of tomographic luminance images corresponding to the plurality of polarization-sensitive tomographic images, based on the detected movement.

An image processing method according to the present invention includes: a step to acquire a plurality of polarization-sensitive tomographic images of an eye; a step to extract a predetermined region from the plurality of polarization-sensitive tomographic images; a step to detect motion of the eye in the plurality of polarization-sensitive tomographic images, based on the extracted predetermined region; and a step to position a plurality of tomographic luminance images corresponding to the plurality of polarization-sensitive tomographic images, based on the detected movement.

Further features of the present invention will become apparent from the following description of exemplary embodiments with reference to the attached drawings.

BRIEF DESCRIPTION OF DRAWINGS

FIG. 3 is a flowchart for describing a photography method according to the first embodiment.

DESCRIPTION OF EMBODIMENT

In a case where the layered structure at the fundus changes due to a disorder or the like, and the spaces between the layers become smaller, a predetermined layer may not be able to be correctly detected. If the layer which was not detected correctly is used to position multiple tomographic images, the accuracy of positioning by deteriorate. Accordingly, it has been found desirable to accurately perform positioning of multiple tomographic images. According to an embodiment, movement of an eye is detected using multiple polarization-sensitive tomographic images of the eye, and multiple tomographic luminance images corresponding to the multiple polarization-sensitive tomographic images can be positioned based on the detected motion. Accordingly, positioning of multiple tomographic images can be accurately performed. A photography apparatus according to the present invention can be applied to objects such as eyes, skin, internal organs, and so forth. Examples of photography apparatuses according to the present invention include ophthalmologic apparatuses, endoscopes, and so forth. An ophthalmologic apparatus according to an embodiment will be described in detail with reference to the drawings, as an example of the present invention.

Overall Configuration of Apparatus

Figure 1:
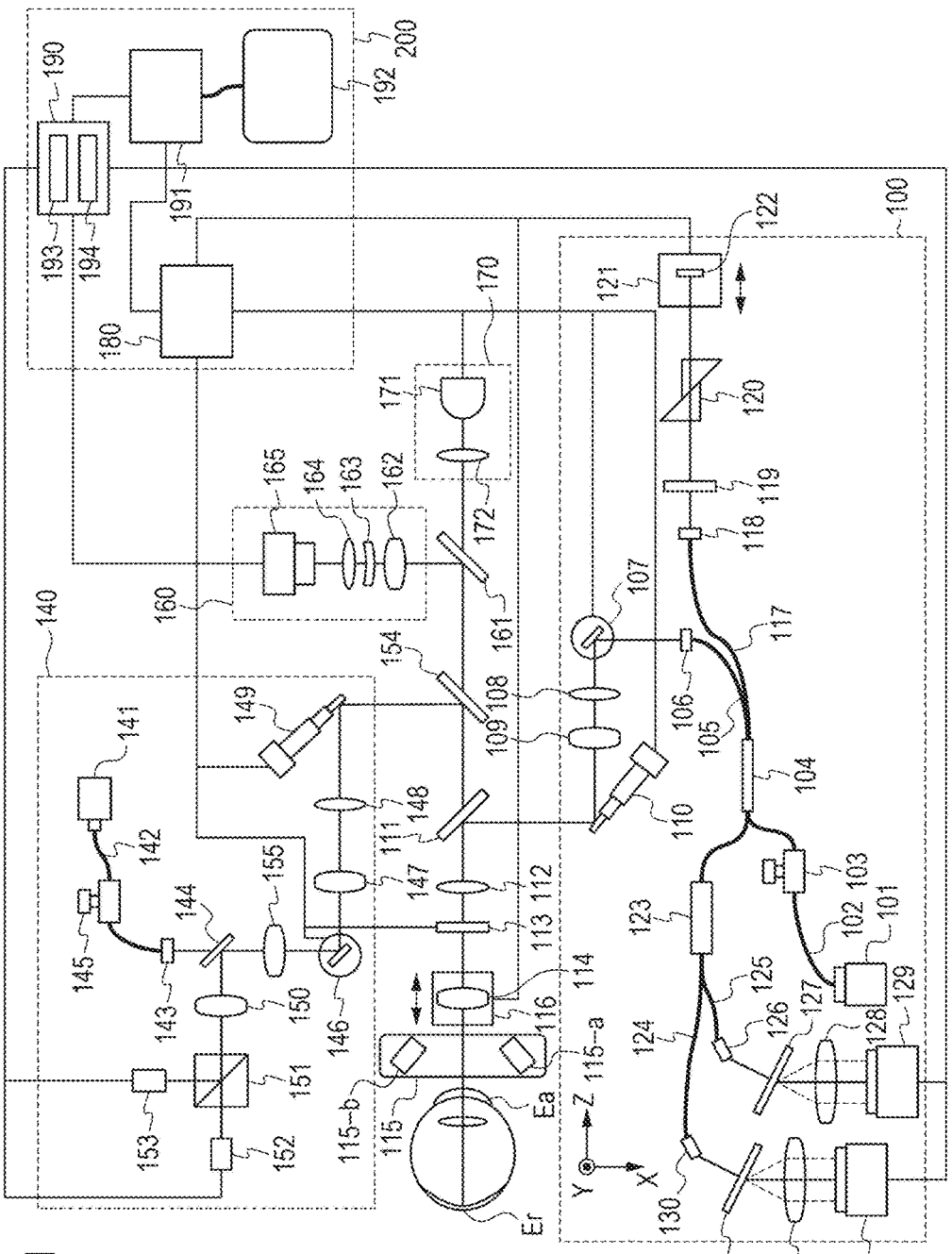
FIG. 1 is a schematic diagram of the overall configuration of a tomographic image apparatus photography apparatus according to a first embodiment.

FIG. 1 is a schematic diagram illustrating the overall configuration of an ophthalmologic imaging apparatus according to the present embodiment. At least part of a later-described signal processing unit 190 can be deemed to be an "image processing apparatus", in which case the overall "ophthalmologic apparatus" can be deemed to be an "ophthalmologic system", and the overall "photography apparatus" can be deemed to be a "photography system".

The present apparatus is configured including a polarization sensitive OCT (PS-OCT) apparatus 100, a polarization sensitive scanning laser ophthalmoscope (PS-SLO) 140 which uses polarized light, an anterior ocular segment imaging unit 160, an interior fixation lamp 170, and a control unit 200.

In a state where the interior fixation lamp 170 is turned on and the eye gazing the interior fixation lamp 170, alignment of the apparatus is performed using an anterior ocular segment image of the eye as observed by the anterior ocular segment imaging unit 160. After alignment is completed, fundus imaging is performed by the PS-OCT apparatus 100 and PS-SLO 140.

Configuration of PS-OCT Apparatus 100

The configuration of the PS-OCT apparatus 100 will now be described. A light source 101 is a super luminescent diode (SLD) light source which is a type of low-coherence light source. The light source 101 emits light having a center wavelength of 850 nm and a bandwidth of 50 nm, for example. Although an SLD is described as being used for the light source 101, any light source capable of emitting low-coherence light may be used, such as an amplified spontaneous emission (ASE) light source, for example.

The light emitted from the light source 101 is guided to a fiber coupler 104 having polarization-maintaining functions, via a PM fiber 102 and polarization controller 103, and splits into measurement light (hereinafter also referred to as "tomographic image measurement light" or "OCT measurement light"), and reference light corresponding to the measurement light.

The polarization controller 103 adjusts the state of polarization of the light emitted from the light source 101 so as to be adjusted to linearly-polarized light. The branching ratio at the fiber coupler 104 is reference light 90 to measurement light 10.

The measurement light is emitted as parallel light from a collimator 106 via a PM fiber 105. The emitted measurement light passes through an X-scanner 107 made up of a galvano mirror which scans the measurement light in the horizontal direction at a fundus Er, lenses 108 and 109, and a Y-scanner 110 made up of a galvano mirror which scans the measurement light in the vertical direction at the fundus Er, and reaches a dichroic mirror 111. The X-scanner 107 and Y-scanner 110 are controlled by a driving control unit 180, and can scan measurement light over a predetermined range of the fundus Er. Note that the range on the fundus Er where the measurement light is scanned can be deemed to be an acquisition range of a tomographic image, an acquisition position of a tomographic image, and a light-casting position for measurement light. The X-scanner 107 and Y-scanner 110 are examples of scanning units for PS-OCT, and may be configured as a common X-Y scanner. The dichroic mirror 111 has properties where light of 800 nm to 900 nm is reflected, and other light is transmitted.

The measurement light reflected by the dichroic mirror 111 passes via a lens 112 and through a λ/4 polarization plate 113 inclined at a 45 degrees angle as from p-polarized light to s-polarized light with the optical axis as the rotational axis. Thus the phase is shifted by 90 degrees, so the polarization of the light is controlled to be circularly-polarized light. Note that the term "p-polarized light" as used in the present specification is light which vibrates horizontally as to the face of incidence when the polarization splitting face of the polarization beam splitter is the reflecting face. S-polarized light is light which vibrates perpendicularly to the face of incidence. Note that the λ/4 polarization plate 113 is an example of a polarization adjusting member for the measurement light, to adjust the polarization state of the measurement light. In a case of applying a later-described PS-SLO optical system, the λ/4 polarization plate 113 can be provided on a common optical path with a part of a PS-OCT optical system and a part of the PS-SLO optical system. Accordingly, variance in the polarization state occluding in images obtained by the PS-SLO optical system and images obtained by the PS-OCT optical system can be relatively suppressed. A scanning unit for PS-SLO and a scanning unit for PS-OCT are situated in conjugate positions, and can be situated at positions conjugate with the pupil of the eye. Note that the inclination of the λ/4 polarization plate 113 is one example of the state of the λ/4 polarization plate 113, and is an angle from a predetermined position, with the optical axis of the polarization splitting face of a fiber coupler 123 including a polarization beam splitter serving as the rotational axis.

The λ/4 polarization plate 113 also can be configured to be extractably inserted to the optical path. For example, a mechanical configuration where the λ/4 polarization plate 113 is rotated on the optical axis or an axis parallel to the optical axis can be conceived. This can realize a small apparatus in which the SLO optical system and PS-SLO optical system can be easily switched between. Also, this can realize a small apparatus in which the OCT optical system and PS-OCT optical system can be easily switched between.

Now, the light input to the eye has the polarization thereof controlled to be circularly-polarized light by the λ/4 polarization plate 113 being installed at a 45 degree angle. However, there are cases where the light is not circularly-polarized light at the fundus Er, due to properties of the eye. Accordingly, the λ/4 polarization plate 113 is configured such that the inclination thereof can be fine-adjusted under control of the driving control unit 180.

The measurement light of which the polarization has been controlled to be circularly-polarized light is focused on a retina layer of the fundus Er by a focus lens 114 on a stage 116, via an anterior ocular segment Ea which is the object. The measurement light cast upon the fundus Er is reflected/scatter at each retina layer, and returns on the optical path to the fiber coupler 104.

The reference light which has branched at the fiber coupler 104 passes through a PM fiber 117 and is emitted from a collimator 118 as parallel light. The emitted reference light is subjected to polarization control by a λ/4 polarization plate 119 inclined at a 22.5 degrees angle as from p-polarized light to s-polarized light with the optical axis as the rotational axis, in the same way as the measurement light. Note that the λ/4 polarization plate 119 is an example of a polarization adjusting member for the reference light, to adjust the polarization state of the reference light. The reference light passes through a dispersion compensation glass 120, is reflected at a mirror 122 on a coherence gate stage 121, and returns to the fiber coupler 104. The reference light passes through the λ/4 polarization plate 119 twice, whereby linearly-polarized light returns to the fiber coupler 104.

The coherence gate stage 121 is controlled by the driving control unit 180 to deal with difference in the axial length of the eye of the subject, and so forth. Note that a coherence gate is a position corresponding to the optical path length of the reference light in the optical path of the measurement light. While the optical path length of the reference light is changed in the present embodiment, it is sufficient that the optical path length difference between the optical path of the measurement light and the optical path of the reference light is changeable.

The return light which has returned to the fiber coupler 104 and the reference light are multiplexed to form interference light (hereinafter also referred to as "multiplexed light"), which is input to a fiber coupler 123 including a polarization beam splitter, and split into p-polarized light and s-polarized light which have different polarization directions, at a branching ratio of 50 to 50.

The p-polarized light passes through a PM fiber 124 and collimator 130, is dispersed at grating 131, and received at a lens 132 and line camera 133. In the same way, the s-polarized light passes through a PM fiber 125 and collimator 126, is dispersed at grating 127, and received at a lens 128 and line camera 129. Note that the grating 127 and 131, and line cameras 129 and 133 are positioned in accordance to each polarization direction.

The light received at each of the line cameras 129 and 133 is output as electric signals in accordance to the intensity of light, and received at the signal processing unit 190 which is an example of a layer image generating unit.

The inclination of the λ/4 polarization plates 113 and 119 can be automatically adjusted with reference to the inclination of the polarization splitting face of the polarization beam splitter included in the fiber coupler 123. Alternatively, automatic adjustment may be made as to a line connecting the center of the optic disc and the center of the macula. At this time, an inclination detector (not illustrated) which detects the inclination of the λ/4 polarization plates 113 and 119 is preferably provided. This inclination detector can detect the current inclination and when reaching a predetermined inclination. Of course, the degree of inclination of the λ/4 polarization plates 113 and 119 can be detected based on the intensity of light that has been received, and adjusted so that the intensity is a predetermined intensity. Also, as described later, the user may display objects indicating inclination on a graphical user interface (GUI) and perform adjustments using a mouse. Also, the same effects can be obtained by adjusting the polarization beam splitter and λ/4 polarization plates 113 and 119 with the vertical direction as the reference.

Configuration of PS-SLO 140

The configuration of the PS-SLO 140 will now be described. A light source 141 is a semiconductor layer which emits light having a center wavelength of 780 nm, for example, in the present embodiment. The measurement light emitted from the light source 141 (hereinafter also referred to as "measurement light for fundus image" or "SLO measurement light") passes through a PM fiber 142, the polarization thereof is controlled at a polarization controller 145 so as to become linearly-polarized light, and is output from a collimator 143 as parallel light. The emitted measurement light passes through the perforation of a perforated mirror 144, passes through a lens 155, passes through an X-scanner 146 made up of a galvano mirror which scans the measurement light in the horizontal direction at a fundus Er, lenses 147 and 148, and a Y-scanner 149 made up of a galvano mirror which scans the measurement light in the vertical direction at the fundus Er, and reaches a dichroic mirror 154. The X-scanner 146 and Y-scanner 149 are controlled by the driving control unit 180, and can scan measurement light over a predetermined range of the fundus Er. The X-scanner 146 and Y-scanner 149 are examples of scanning units for PS-SLO, and may be configured as a common X-Y scanner.

The dichroic mirror 154 has properties where light of 760 nm to 800 nm is reflected, and other light is transmitted.

The linearly-polarized light measurement light reflected at the dichroic mirror 154 passes over the same optical path as with the PS-OCT apparatus 100, and reaches the fundus Er.

The measurement light which has been cast on the fundus Er is reflected/scatter at the fundus Er, and returns on the above-described optical path to reach the perforated mirror 144. The light reflected at the perforated mirror 144 passes through a lens 150 and is input to a polarization beam splitter 151, and split into light which have different polarization directions (p-polarized light and s-polarized light in the present embodiment), received at avalanche photodiodes (APD) 152 and 153 and converted into electric signals, which are received at the signal processing unit 190 which is an example of a fundus image generating unit.

The position of the perforated mirror 144 is conjugate with the pupil position of the eye. Of the measurement light cast on the fundus Er and reflected/scattered, the light which has passed through around the pupil is reflected by the perforated mirror 144.

While PM fibers have been used for both the PS-OCT apparatus and PS-SLO in the present embodiment, the same configuration and effects can be obtained by controlling polarization using a polarization controller even if using single mode fiber (SMF).

Anterior Ocular Segment Imaging Unit 160

The anterior ocular segment imaging unit 160 will now be described. The anterior ocular segment imaging unit 160 illuminates the anterior ocular segment Ea using an illumination light source 115 including LEDs 115-a and 115-b which emit illumination light having a wavelength of 1000 nm. The light reflected at the anterior ocular segment Ea passes through the lens 114, polarization plate 113, lens 112, dichroic mirrors 111 and 154, and reaches a dichroic mirror 161. The dichroic mirror 161 has properties where light of 980 nm to 1100 nm is reflected, and other light is transmitted. The light reflected at the dichroic mirror 161 passes through lenses 162, 163, and 164, and is received at an anterior ocular segment camera 165. The light received at the anterior ocular segment camera 165 is converted into electric signals, and received at the signal processing unit 190.

Interior Fixation Lamp 170

The interior fixation lamp 170 will now be described. The interior fixation lamp 170 is configured including an interior fixation lamp display unit 171 and a lens 172. The interior fixation lamp display unit 171 includes multiple light-emitting diodes (LEDs) arrayed in a matrix. The lighting position of the LEDs is changed in accordance with the region to be imaged, under control of the driving control unit 180. Light from the interior fixation lamp display unit 171 is guided to the eye via the lens 172. The light emitted from the interior fixation lamp display unit 171 has a wavelength of 520 nm, and a desired pattern is displayed by the driving control unit 180.

Control Unit 200

The control unit 200 which controls the overall apparatus will now be described. The control unit 200 includes the driving control unit 180, the signal processing unit 190, a display control unit 191, and a display unit 192. The driving control unit 180 controls each part as described above.

The signal processing unit 190 includes an image generating unit 193, and an image analyzing unit 194. The signal processing unit 190 generates images, analyzes the generated images, and generates visualization information of the analysis results, based on signals output from each of the line cameras 129 and 133, APDs 152 and 153, and anterior ocular segment camera 165. Details of generating and analyzing images will be described later.

The display control unit 191 displays images generated and acquired at the tomographic image generating unit and fundus image generating unit, by a fundus image acquiring unit (not illustrated) and a tomographic image acquiring unit (not illustrated), and so forth, on a display screen of the display unit 192. The display unit 192 here is a liquid crystal display or the like. The image data generated at the signal processing unit 190 may be transmitted to the display control unit 191 by cable, or wirelessly. In this case, the display control unit 191 can be deemed to be an image processing apparatus, and it is sufficient that the image processing apparatus and photography apparatus (ophthalmologic apparatus) are communicably connected. An arrangement may be made for the photography system where a fundus image acquisition unit includes an SLO optical system, and a tomographic image acquisition unit includes an OCT optical system. In the present Specification, if the object is other than an eye, the term "fundus image (fundus luminesce image)" can be rephrased as "planar image "planar luminesce image)", and the term "fundus image acquisition unit" can be rephrased as "planar image acquisition unit".

The display unit 192 displays various types of information in various display formats under control of the display control unit 191, as described later. The image data from the display control unit 191 may be transmitted to the display unit 192 by cable, or wirelessly. While the display unit 192 and other units are illustrated as being included in the control unit 200, but the present invention is not restricted to this, and may be provided separately from the control unit 200. Also, the display control unit 191 and display unit 192 may be integrally formed as a tablet, which is an example of a device which can be carried by the user. In this case, the display unit preferably has a touch panel function, so that the display position can be moved, enlarged, or reduced, and the displayed image can be changed, or the like, by performing operations on the touch panel.

Image Processing

Next, image generating at the image generating unit 193 included in the signal processing unit 190 will be described. The image generating unit 193 performs reconstruction processing commonly used in spectral domain (SD) OCT on interference signals output from the line cameras 129 and 133, thereby generating two tomographic images based on each polarization component. The two tomographic images are a tomographic image corresponding to first polarization light, and a tomographic image corresponding to second polarization light.

First, the image generating unit 193 removes fixed pattern noise from the interference signals. Removal of the fixed pattern noise is performed by extracting the fixed pattern noise by averaging multiple A-scan signals that have been detected and subtracting the fixed pattern noise from the input interference signals.

Next, the image generating unit 193 converts the interference signals from wavelength to wavenumber, and performs Fourier transform, thereby generating tomography signals representing the polarization state.

Performing the above-described processing on the interference signals of the two polarization components generates two tomographic images.

The image generating unit 193 arrays the signals output from the APDs 152 and 153 synchronously with the driving of the X-scanner 146 and Y-scanner 149, thereby generating two fundus images based on the respective polarization components. The two fundus images are a fundus image corresponding to the first polarization light, and a fundus image corresponding to the second polarization light.

Generating Tomographic Luminance Image or Fundus Luminance Image

The image generating unit 193 generates a tomographic luminance image from the two aforementioned tomography signals. The tomographic luminance image is basically the same as a tomographic images in conventional OCT. A pixel value r thereof is calculated from tomography signals $A_H$ and $A_V$ obtained from the line sensors 129 and 133, as calculated by Expression (1).

[Math. 1]

$$r = \sqrt{A_H^2 + A_V^2}$$ 
Expression (1)

A fundus luminance image is also generated from the two fundus images in the same way.

Figure 2E:
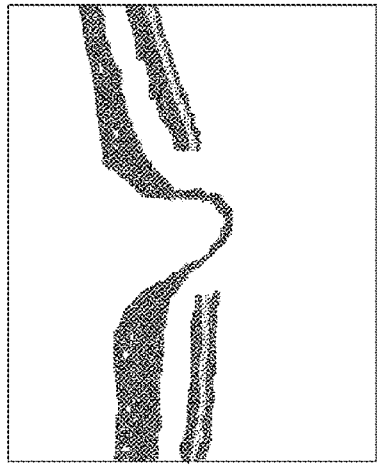
FIGS. 2A through 2E are examples of images generated at a signal processing unit according to the first embodiment.
Figure 2B:
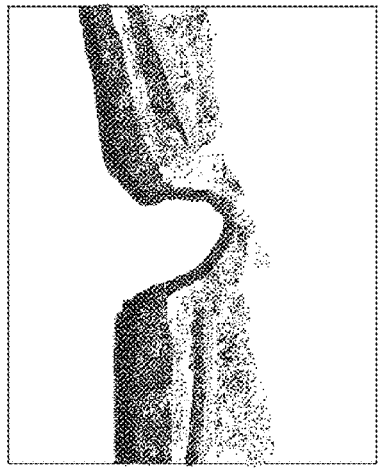
Figure 2D:
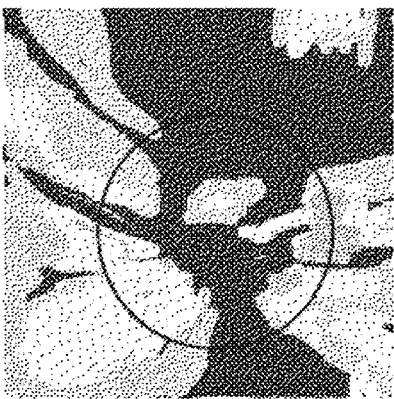
Figure 2A:
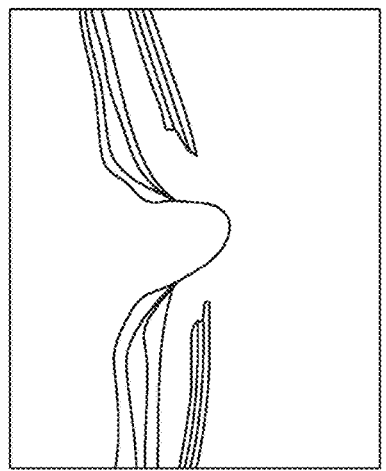

FIG. 2A illustrates an example of a luminance image of an optic disc. The display control unit 191 may display a tomographic luminance image acquired by conventional OCT techniques on the display unit 192 in a case where the λ/4 polarization plate 113 has been evacuated from the optical path, or may display a fundus luminance image acquired by conventional SLO techniques on the display unit 192.

Generating Retardation Image

The image generating unit 193 generates retardation images from tomographic images of mutually orthogonal polarization components. A value δ of each pixel of the retardation image is a value representing the ratio of influence which the vertical polarization component and horizontal polarization component receive at the eye, at the position of each pixel in the tomographic image. The value δ is calculated from the tomography signals $A_H$ and $A_V$ by the following Expression (2).

[Math. 2]

$$\delta = \arctan\left[\frac{A_V}{A_H}\right]$$ 
Expression (2)

FIG. 2B illustrates an example of a retardation image of the optic disc generated in this way, and can be obtained by performing calculation according to Expression (2) on each B-scan image. As described earlier, a retardation image is a tomographic image indicating the difference in influence which the two polarization components received at the eye. FIG. 2B is a color display to values representing the above ratio as a tomographic image. Dark portions indicate a small value for the ratio, and light portions indicate a great value for the ratio. Accordingly, layers with birefringence can be comprehended by generating a retardation image. Details are described in NPL 1.

The signal processing unit 190 can generate a retardation image in the planar direction of the fundus, based on output from the APDs 152 and 153 in the same way.

Generating Retardation Map

The image generating unit 193 generates a retardation map from the retardation image obtained with regard to multiple B-scan images. The image generating unit 193 detects the retinal pigment epithelium (RPE) in each B-scan image. The RPE has a nature of cancelling polarized light, so retardation distribution is inspected in each A-scan image in the depth direction, from the inner limiting membrane (ILM) over a range not including the RPE. The maximum value thereof is the representative value of retardation in the A-scan.

The image generating unit 193 performs the above processing on all retardation images, thereby generating a retardation map.

Figure 2C:
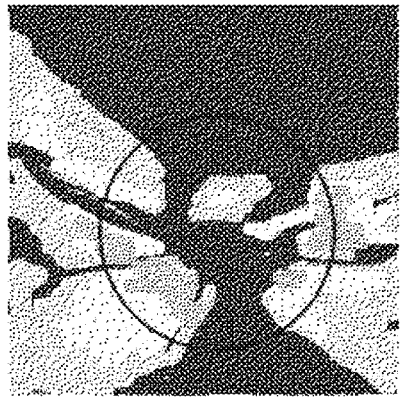

FIG. 2C illustrates an example of a retardation map of the optic disc. Dark portions indicate a small value for the aforementioned ratio, and light portions indicate a great value for the aforementioned ratio. The retinal nerve fiber layer (RNFL) is a layer having birefringence at the optic disc. The retardation map is an image illustrating the difference in influence which the two polarized lights receive due to the birefringence of the RNFL and the thickness of the RNFL. Accordingly, the value indicating the aforementioned ratio is great when the RNFL is thick, and the value indicating the aforementioned ratio is small when the RNFL is thin. Accordingly, a retardation map allows the thickness of the RNFL of the entire fundus to be comprehended, which can be used in diagnosis of glaucoma.

Generating Birefringence Map

The image generating unit 193 linearly approximates the value of retardation δ in the range of the ILM to the RNFL, in each A-scan image of the retardation images generated earlier, and determines the inclination thereof to be the birefringence at the position of the A-scan image on the retina. That is to say, the retardation is the product of distance and birefringence in the RNFL, so a linear relation is obtained by plotting the depth and retardation values in each A-scan image. Accordingly, this plot is subjected to linear approximation by the method of least squares, and the inclination is obtained, which is the value for birefringence of the RNFL in this A-scan image. This processing is performed on all retardation images that have been acquired, thereby generating a map representing birefringence.

FIG. 2D illustrates an example of a birefringence map of the optic disc. The birefringence map directly maps birefringence values, so even if the thickness of the RNFL does not change, change in the fiber structure thereof can be visualized as change in birefringence.

Generating a DOPU Image

The image generating unit 193 calculates a Stokes vector S for each pixel, from the obtained tomography signals $A_H$ and $A_V$, and the phase difference $\Delta\Phi$ therebetween, by the following Expression (3),

[Math. 3]

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix} \quad \text{Expression (3)}$$

where $\Delta\Phi$ has been calculated from $\Delta\phi = \phi_V - \phi_H$, from the phases $\phi_H$ and $\phi_V$ of each signal obtained at the time of calculating the two tomographic images.

The image generating unit 193 sets a window for each B-scan image of a size around 70 μm in the main scanning of the measurement light and 18 μm in the depth direction, averages each element of the Stokes vector calculated for each pixel by Expression (3) within each window, and calculates the degree of polarization uniformity (DOPU) in each window by Expression (4),

[Math. 4]

$$DOPU = \sqrt{Qm^2 + Um^2 + Vm^2} \quad \text{Expression (4)}$$

where $Q_m$, $U_m$, and $V_m$ are each values of the averaged Stokes vector elements Q, U, and V in each window.

This processing is performed on all windows within the B-scan image, thereby generating a DOPU image of the optic disc illustrated in FIG. 2E. AS described above, a DOPU image is a tomographic image indicating the uniformity of the two polarized lights.

DOPU is a numerical value representing uniformity of polarized light. At locations where polarization is maintained, the value is near 1, and the value is smaller than 1 at regions where polarization light is cancelled, which is an example of a predetermined region (locations where polarization is not maintained). The RPE has a nature of cancelling the polarization state, so the portions in the DOPU image corresponding to the RPE exhibit a smaller value as compared to other regions. The light portion 210 in FIG. 2E represents the RPE, and the dark portion 220 represents the retinal layer region where polarization is maintained. The DOPU image visualizes layers where polarization is cancelled, such as the RPE and so forth, so even in a case where the RPE has been deformed by a disease or the like, the RPE can be visualized in a more sure manner than change in luminance.

Also, in the same way, the signal processing unit 190 can generate a DOPU image in the planar direction of the fundus, based on output from the APDs 152 and 153.

Note that in the present Specification, the above-described tomographic images corresponding to the first and second polarized light, retardation images, DOPU images, and so forth, may also be referred to as "tomographic images indicating polarization state" or "polarization-sensitive tomographic images". Also in the present Specification, the above-described retardation map and birefringence map and so forth may also be referred to as "fundus image indicating polarization state" or "polarization fundus image".

Processing Operations

Next, processing operations according to the image photography apparatus and image processing apparatus will be described with reference to FIG. 3. FIG. 3 is a flowchart illustrating processing operations of the image photography apparatus and image processing apparatus.

Adjustment

First, in step S101, alignment of the apparatus and the eye is performed with the eye set to the apparatus. Description will be made regarding alignment unique to the present specification, and general adjustments such as XYZ alignment of working distance and so forth, focusing, coherence gate adjustment, and so forth will be omitted from description.

Adjustment of PS-OCT Imaging Position

Figure 4:
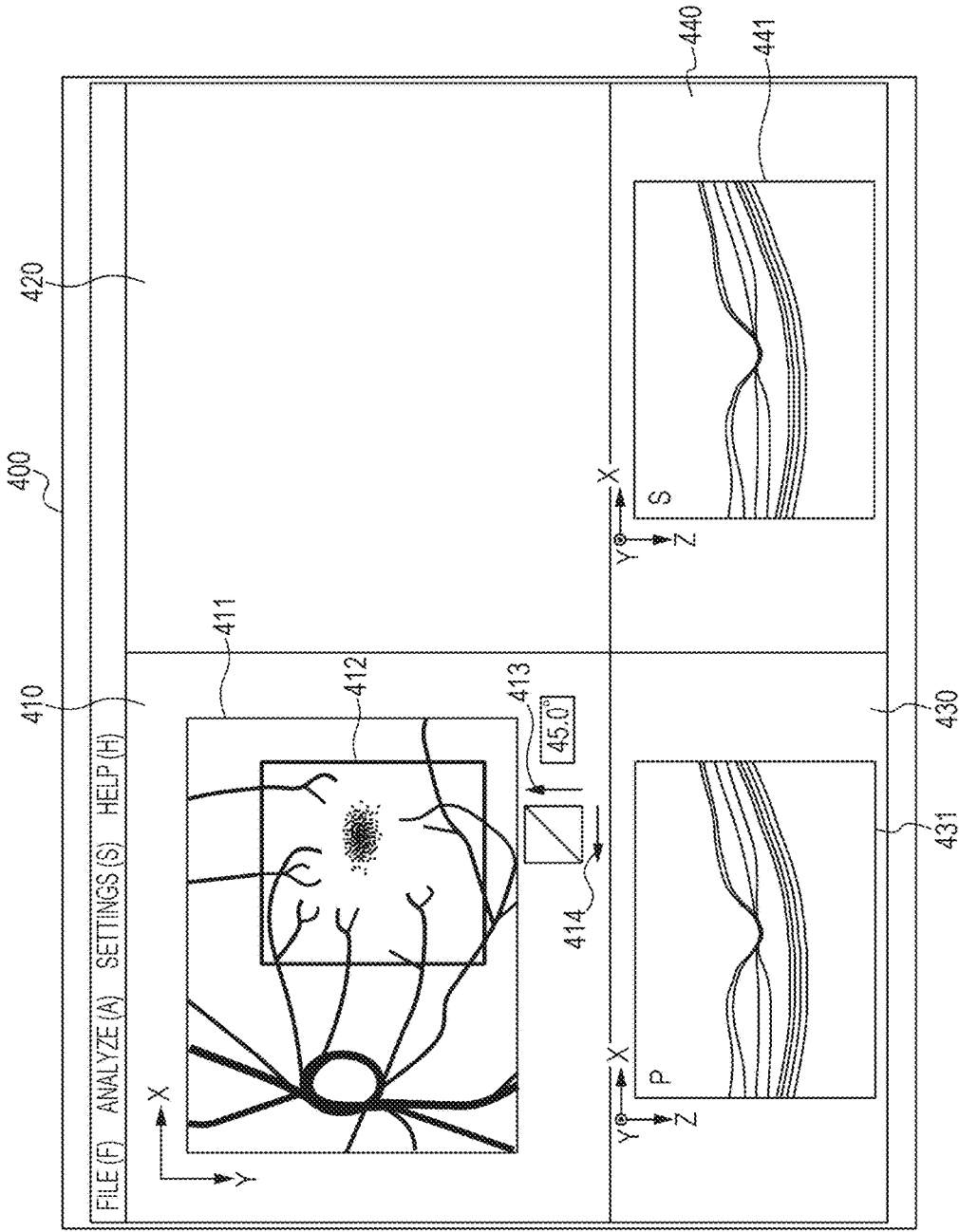
FIG. 4 is a display example of a display screen on a display unit of the tomographic image apparatus photography apparatus according to the first embodiment.

FIG. 4 illustrates a window 400 displayed on the display unit 192 when performing adjustments. A display region 410 which is an example of a first display region displays a fundus image 411 imaged by the PS-SLO 140 and generated by the signal processing unit 190. A frame 412 indicating the imaging range of the PS-OCT apparatus 100 is superimposed thereupon.

The operator sets a photography range by instructing using a cursor displayed in the window 400, by performing clicking and dragging operations and the like on an instruction device such as a mouse or the like (not illustrated), under control of the driving control unit 180. That is to say, the frame 412 can be specified with the cursor, and moved by dragging. Setting of the imaging range is performed by the driving control unit 180 controlling the driving angle of the scanner. Thus, the driving control unit 180 sets the photography range for controlling the driving angle of the scanner. The mouse in this embodiment includes, for example, a sensor to detect motion signals when the mouse is moved two-dimensionally by the hand of the user, two mouse buttons, left and right, to detect pressing by the hand of the user, and a wheel mechanism which is provided between the two left and right mouse buttons and which can be rotated forwards and backwards. The instruction device may be such that a display unit is provided with touch panel functions, so that acquisition positions are specified on the touch panel.

Adjustment of λ/4 Polarization Plate

Adjustment of the λ/4 polarization plate 113 will be described. In FIG. 4, instruction portions 413 and 414 are displays to adjust the angle of the λ/4 polarization plate 113. The angle of the λ/4 polarization plate 113 is adjusted by the operating giving instructions using the instruction device, under control of the driving control unit 180. The instruction portion 413 is a display for instructing adjustment in the counter-clockwise direction, and the instruction portion 414 is a display for instructing adjustment in the clockwise direction. The numerical value displayed to the side of the instruction portions 413 and 414 indicates the current angle of the λ/4 polarization plate 113. The display control unit 191 may display instruction portions for adjusting the angle of the λ/4 polarization plate 119 alongside the instruction portion 413 on the display unit 192, or instead of the instruction portion 413.

Guiding the cursor by the mouse, the operator input instructions so that the luminance of each polarized light tomographic image displayed in a display region 430 which is an example of a third display region, and a display region 440 which is an example of a fourth display region, are the same. This may be done by displaying the peak luminance values of the tomographic images 431 and 441 of the respective polarized lights, or by displaying waveforms themselves of the interference signals, and the operator viewing these and performing adjustment. Here, the tomographic images 431 and 441 of the respective polarized lights are examples of a tomographic image corresponding to first polarized light and a tomographic image corresponding to second polarized light. The tomographic images 431 and 441 (or later-described tomographic images 531 and 541) of the respective polarized lights preferably are of a display format indicating the type of image, such as "P" indicating p-polarized light and "S" indicating s-polarized light being superimposed on the images, for example. This helps to prevent the user from misidentifying the images. Of course, this display may be made above or to the side of the images instead of being superimposed, as long as correlated with the images.

A display region 420 which is an example of a second display region may display nothing at this stage, or in the case of automatic adjustment or the like may display a message such as "Currently adjusting λ/4 polarization plate" or the like to indicate the current adjustment state. Also, the window 400 may display patient information such as the eye and the other eye of the left and right eyes, photography information such as the photography mode and so forth, or the like. The λ/4 polarization plate 113 is preferably repetitively inserted into and evacuated from the optical path, so as to alternately obtain fundus luminance images and tomographic images indicating polarization state. This enables the display control unit 191 to display a fundus luminance image in the display region 410, and then display a tomographic image indicating polarization state in the display region 420, for example, using an ophthalmologic apparatus of which the size is minimal.

The order of adjustment preferably is alignment adjustment using anterior ocular segment images or corneal bright points, focus adjustment using fundus images indicating polarization state, coherence gate adjustment using tomographic images indicating polarization state, and adjustment of the λ/4 polarization plate 113. While the acquisition position of the tomographic image indicating polarization state is preferably decided before the coherence gate adjustment using tomographic images indicating polarization state, this may be decided in initial settings so as to acquire the center region of the fundus image indicating polarization state. Accordingly, tomographic images indicating polarization state which can handle finer and narrower ranges than fundus images indicating polarization state can be accurately acquired by simple adjustment. At this time, the λ/4 polarization plate 113 may be automatically adjusted in accordance with completion of the coherence gate adjustment, or the λ/4 polarization plate 113 may be automatically adjusted in accordance with input of a signal to acquire an image indicating polarization state. Of course, a configuration may be made where the λ/4 polarization plate 113 is adjusted beforehand at the initial settings screen or the like upon startup of the ophthalmologic apparatus, and not adjusted each time photography is performed.

In a case where the λ/4 polarization plate 113 is configured to be inserted and evacuated from the optical path, the order of adjustment preferably is alignment adjustment using anterior ocular segment images or corneal bright points, focus adjustment using SLO fundus images, coherence gate adjustment using OCT tomographic images, insertion of the λ/4 polarization plate 113 into the optical path, and adjustment of the λ/4 polarization plate 113. Thus, adjustment before acquiring images indicating polarization state can be performed using normal SLO fundus images and OCT tomographic images which the user is intuitively familiar with. Alternatively, the λ/4 polarization plate 113 may be inserted after focus adjustment, and thereafter coherence gate adjustment performed using a PS-OCT tomographic image indicating polarization state. In this case, the λ/4 polarization plate 113 may be automatically inserted into the optical path in accordance with completion of the coherence gate adjustment or completion of focus adjustment, or the λ/4 polarization plate 113 may be automatically inserted into the optical path in accordance with input of a signal to acquire an image indicating polarization state.

The focus adjustment may be performed such that rough focus adjustment is first performed using an SLO fundus image, and thereafter fine focus adjustment is performed using an OCT tomographic image.

These adjustments may be performed in the above-described order automatically, or sliders may be displayed on the display unit corresponding to each adjustment, and the cursor used to perform drag operations for adjustment. In a case of inserting/evacuating the λ/4 polarization plate 113, icons to insert the λ/4 polarization plate 113 into the optical path, and to evacuate, may be displayed on the display unit.

Imaging Through Generating Images

In steps S102 and S103, measurement light is emitted from the light source 101, light source 141, and return light from the fundus Er is received at line cameras 129 and 133 and APDs 152 and 153, so as to generate the images at the image generating unit 193 as described above. In the present embodiment, an N number of B-scan images, each made up of an M number of A-scans, are generated by controlling the X-scanner 110 and Y-scanner 107. M and N can be set from the time necessary for shooting and the size of the region necessary for diagnosis, but for example, around M=1024 and N=250 may be set as to a region of 8 mm×6 mm centered on a macula.

Analysis

There are cases where the luminance value of tomographic images is darker in diseased eyes due to the disease, as compared to tomographic images of healthy eyes. This may lead to missing finding the retina layer, or erroneous detection. Accordingly, in step S104, the image analyzing unit 194 detects the layers of the retina using information of locations (regions) where the polarization state is cancelled, which has been calculated by the image generating unit 193 in step S103.

The RPE cancels the polarization state in the retina layer, so calculating the DOPU in Expression (4) allows the position of the PRE 210 to be detected. Further, the overall retina layer 220 which does not cancel the polarization state can be detected. Accordingly, the luminance value of the RPE can be found for each tomographic image, by referencing the luminance value of each location in the luminance image corresponding to the RPE. Accordingly, even if the luminance value of tomographic images is overall darker due to disease, the region of the overall retina, and the position of the RPE and luminance values corresponding to the PRE can be found, so cases of missing detection and erroneous detection due to disease can be reduced.

An example of a method to detect the boundary of the layers of the retina is to use the luminance value obtained from the position calculated by DOPU in Expression (4) as a threshold value for layer detection. For example, a threshold value to be used to find the boundary of each layer in a healthy eye is set beforehand. The average luminance value of the RPE and the overall retina layer region is also set beforehand. The luminance value of the RPE from the position obtained by calculating Expression (4), the luminesce value of the overall retina layer region, and the average luminance value set beforehand, are compared. The threshold to be used to obtain the boundaries of the layers set beforehand is adjusted depending on how many percent the difference in luminance value is. For example, in a case where the luminance value of the luminance image corresponding to the RPE 210 and retina layer region 220 in FIG. 2E is 10% lower than the average luminance set beforehand, the threshold is lowered by 10%. The image analyzing unit 194 then applies a median filter which is a type of averaging, and a Sobel filter, which is a type of edge detection, to the tomographic image to be processed, and creates images by each (hereafter also referred to as "median image" and "Sobel image"). Next, a profile is created for each A scan, from the created median image and Sobel image. A luminance value profile is created from the median image, and a gradient profile is created from the Sobel image. Peaks are detected in the profile created from the Sobel image. The profile of the median image corresponding to nearby the detected peaks or between the peaks is referenced, and compared with the threshold obtained earlier, whereby the regions of the retina layer or the boundaries thereof can be extracted. For example, the image analyzing unit 194 extracts the RNFL, inner limiting membrane, and photoreceptor inner segment/outer segment (IS/OS) junction, from the retardation image. The image analyzing unit 194 also extracts the RPE from the DOPU image.

The processing of steps S102 through S104 is repeated N times, thereby acquiring N tomographic images. The operator may optionally decide the acquiring procedures at this time. That is to say, steps S103 and S104 may be performed in batch fashion after having repeated step S102 N times and obtained the data of N tomographic images, or steps S102 through S104 may be performed in order for each acquisition of a tomographic image, and this may be repeated N times.

Positioning

Figure 5A:
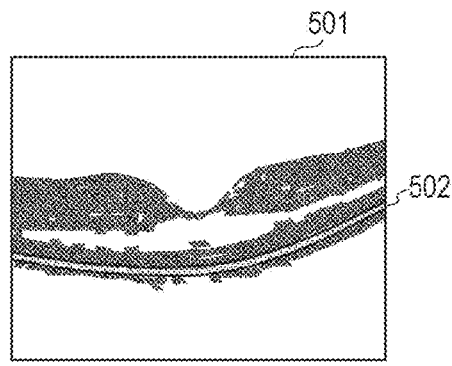
FIGS. 5A and 5B are diagrams for describing tomographic images according to the first embodiment.
Figure 5B:
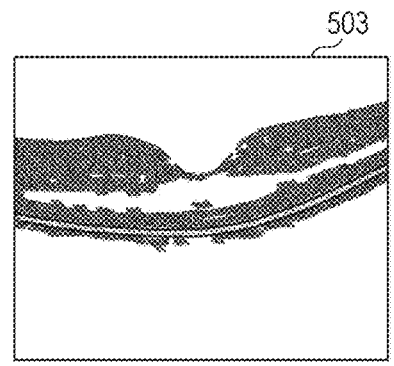

A case will now be considered for positioning tomographic images using DOPU images in step S105, after having extracted N DOPU images in step S104. In the present embodiment, the tomographic images to be positioned are luminance images. The tomographic images may be selected as necessary. Positioning is performed such that, in FIG. 5 for example, pattern matching of a second DOPU image 503 is performed as to a reference first DOPU image 501, thereby detecting movement of the eye. Pattern matching is a technique to search for a region where similarity as to a reference image is the highest. Pattern matching is performed in the present embodiment using the entire DOPU image 501 to perform pattern matching, but is not restricted to this. An arrangement may be made where a certain portion with a feature is extracted from the first DOPU image serving as a reference, a matching portion is searched for by performing pattern matching as to the second DOPU image, and movement of the eye during the image acquisition time may be detected from the coordinates thereof. For example, pattern matching may be performed using just the light layer 502 in the DOPU image.

The pattern matching is performed at the signal processing unit 190, where the similarities of multiple other DOPU images as to the first DOPU image serving as the reference are calculated. A correlation function may be used for calculating similarity, for example. The operator may optionally select the pattern matching method. Tomographic images of the same location are overlaid in the present embodiment, so in a case of overlaying N tomographic images for example, pattern matching is performed so that each DOPU image of the N−1 DOPU images matches the first DOPU image with the highest degree of similarity. On the other hand, in a case of compositing a three-dimensional image from N tomographic images, matching has to be performed with a DOPU image acquired immediately before. That is to say, a process where pattern matching is performed for a second DOPU image obtained immediately after a first DOPU image, pattern matching is performed for a third DOPU image obtained immediately after the second DOPU image, and so on for N−1 times, has to be performed.

Displaying similarity as a parameter at the time of performing pattern matching enables this to be used as an indicator of whether or not to overlay, when overlaying the tomographic images.

Figure 6:
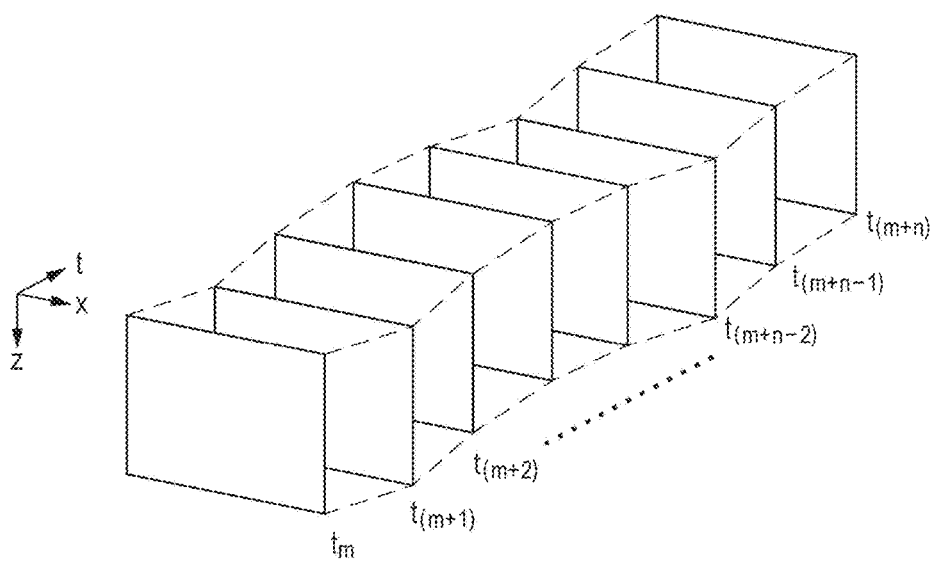
FIG. 6 is a diagram for describing positioning tomographic images according to the first embodiment.

After performing pattern matching, the signal processing unit 190 stores displacement amount regarding movement of the DOPU image which was performed to obtain the highest similarity. For example, in FIG. 6, in a case where (x(m+1), y(m+1)) is amount of displacement of the DOPU image of which the similarity is the highest at time t(m+1), as to the DOPU image at time tm, this displacement (x(m+1), y(m+1)) is stored. The amount of displacement to be stored here is not restricted to parallel movement. For example, the amount of displacement regarding rotation and enlargement/reduction may be stored as necessary. Also, the displacement amount stored in the signal processing unit 190 may be applied to all images obtained at the same timing and generated at the image generating unit 193.

Output of Overlaid Images

Upon positioning of all DOPU images extracted in step S105 having been completed, in step S106 the tomographic images are overlaid at the image generating unit 193 of the signal processing unit 190. The display control unit 191 generates output information based on the results thereof, and outputs to the display unit 192 for display. The overlaying of the tomographic images is performed by compositing the N−1 tomographic images as to the first tomographic image serving as a reference, by positioning the positions of each thereto, based on the displacement amount that has been stored in step S105. The technique of overlaying is a commonly practiced technique, so detailed description thereof will be omitted here.

There is no need to overlay all acquired tomographic images. The operator may optionally decide the number to be overlaid, or an arrangement may be made where a threshold for similarity in pattern matching is provided in step S106 so that only tomographic images at or above the threshold are overlaid.

Figure 7:
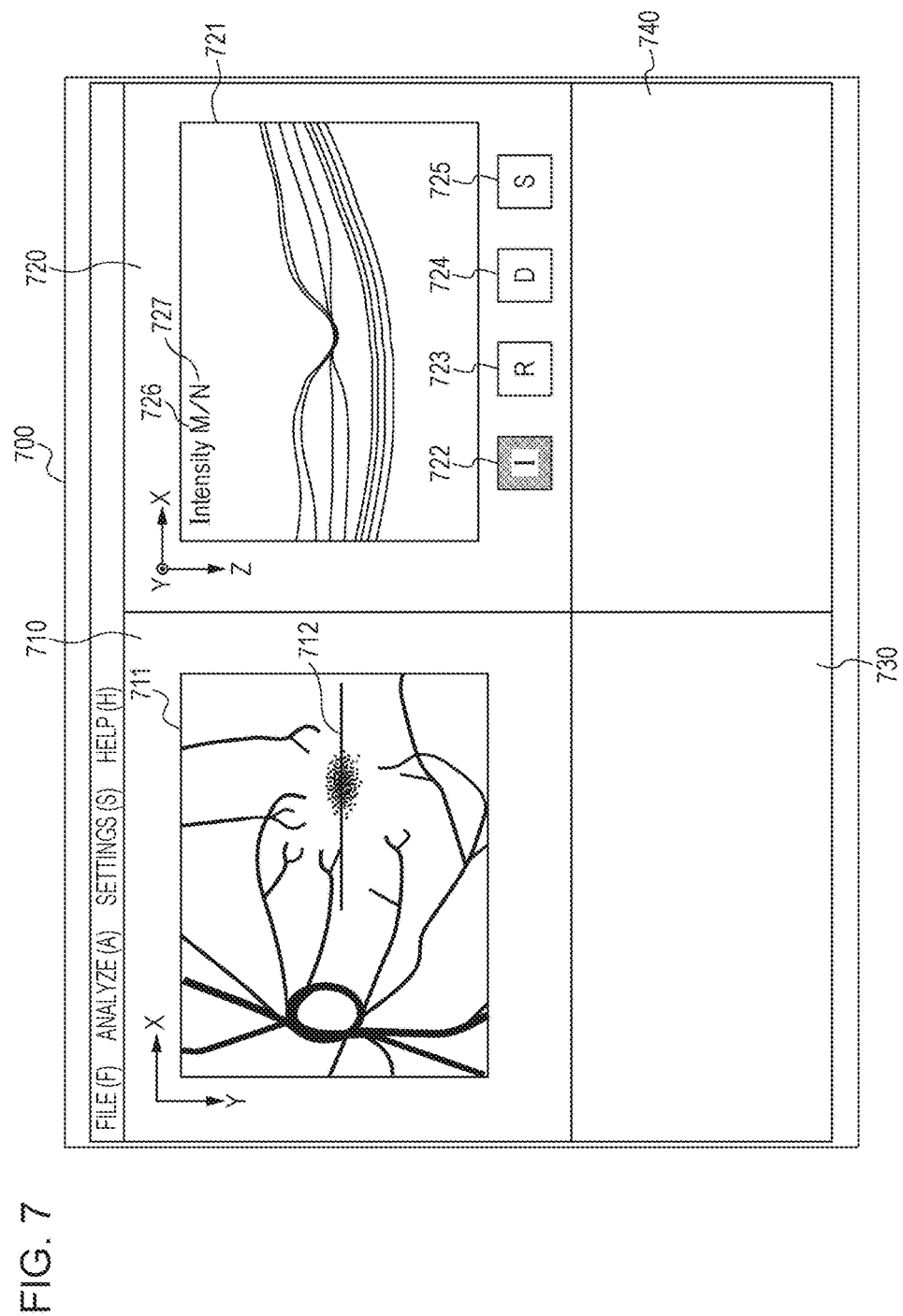
FIG. 7 is a diagram for describing a display screen on the display unit of the tomographic image apparatus photography apparatus according to the first embodiment.

FIG. 7 is a display example on the display unit 192 according to the present embodiment. Reference numeral 700 denotes a window display on the display unit 192, including display regions 710, 720, 730, and 740.

A fundus image 711 is displayed in the display region 710 (also referred to as "first display region"), and a display 712 indicating the position of the tomographic image is superimposed thereupon. A fundus luminance image is displayed here as the fundus image 711, but may be a fundus image based on polarization signals instead.

N overlaid tomographic images (luminance tomographic images) 721 are displayed in the display region 720 (also referred to as "second display region") for selecting the type of tomographic image to be displayed. Also displayed in the display region 720 are buttons 722 through 725 (an example of a selecting unit). Note that the type of tomographic image may be selected from a menu, instead of the buttons 722 through 725.

FIG. 7 illustrates a state in which the button 722 has been selected, which is an example of displaying the results of overlaying luminesce tomographic images. The other buttons 723 through 725, and display thereby, will be described. Upon the operator selecting the button 723, a retardation image is displayed in the display region 720. Selecting the button 724 displays a DOPU image in the display region 720. Selecting the button 725 displays segmentation results superimposed on the luminance tomographic image in the display region 720.

Note that the luminance tomographic image 721, retardation image, DOPU image, segmentation image, and so forth, preferably have the text "Intensity", "Retardation", "DOPU", and "Segmentation", displayed thereupon respectively, to indicate the type of image being displayed. This can prevent the user from misidentifying an image. Of course, the text may be displayed above or to the side, as long as the text and images correspond. Further, the luminance tomographic image 721, retardation image, DOPU image, segmentation image, and so forth, preferably display the number of images overlaid 726, and the number of images shot 727.

As described above, according to the present embodiment, tomographic images acquired by polarization sensitive OCT can be accurately overlaid using DOPU images. Even in a case where the fundus is deformed due to a disease or the like, using DOPU images which have polarization information enables positioning to be performed, so the images can be accurately overlaid.

While description has been made in the present embodiment regarding positioning in the optical axis direction of the measurement light, the present embodiment is not restricted to this, and is applicable to motion within a plane perpendicular to the optical axis of the measurement light. Further, correction of motion within a plane perpendicular to the optical axis of the measurement light can be accurately performed using methods according to the related art. For example, template matching may be performed using feature locations within the fundus image, and the position where the measurement light is cast is corrected in real-time.

The positions in the display region at which to display these images are not restricted to those described in the present embodiment. Neither is the number of images to be displayed restricted to that described in the present embodiment. It is needless to say that the order, positions and so forth of the buttons 722 through 725 are not restricted to those described in the present embodiment.

Also, while description has been made in the present embodiment regarding a case of performing photography of one location N times to overlay tomographic images, the present technology is not restricted to this. For example, the present technology is applicable to a case of changing the acquisition position of tomographic images over time, and acquiring a three-dimensional tomographic image.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-159175, filed Jul. 31, 2013, which is hereby incorporated by reference herein in its entirety.

The invention claimed is:

1. An image processing apparatus comprising:
an extracting unit configured to extract a depolarizing region in a plurality of polarization-sensitive tomographic images of an eye;
a detecting unit configured to detect motion of the eye using the extracted depolarizing region; and a positioning unit configured to position a plurality of tomographic luminance images corresponding to the plurality of polarization-sensitive tomographic images, using the detected movement.

2. The image processing apparatus according to claim 1, wherein the plurality of polarization-sensitive tomographic images are a plurality of degree of polarization uniformity (DOPU) images;

and wherein the extracting unit extracts the retinal pigment epithelium in the plurality of DOPU images, as the depolarizing region.

3. The image processing apparatus according to claim 1, further comprising:

an overlaying unit configured to overlay a plurality of tomographic luminance images which have been positioned; and a display control unit configured to display the overlaid images on a display unit.

4. The image processing apparatus according to claim 1, wherein the detecting unit detects at least one of movement, enlarging/reduction, and rotation, in the plurality of polarization-sensitive tomographic images, as the motion.

5. The image processing apparatus according to claim 1, wherein the plurality of polarization-sensitive tomographic images and the plurality of tomographic luminance images are generated using light having different polarizations, by splitting a combined light obtained by combining return light from the eye irradiated by the measurement light and reference light corresponding to the measurement light.

6. The image processing apparatus according to claim 5, wherein the image processing apparatus is communicably connected to an ophthalmologic apparatus including a detection unit configured to detect the light having polarization different from each other, and wherein the plurality of polarization-sensitive tomographic images and the plurality of tomographic luminance images are generated using the detected light having polarization different from each other.

7. The image processing apparatus according to claim 1, wherein the plurality of polarization-sensitive tomographic images and the plurality of tomographic luminance images are generated using light having different polarizations by splitting a combined light obtained by combining return light from the eye irradiated by the measurement light and reference light corresponding to the measurement light, the light having different polarizations being detected by a detection unit of an ophthalmologic apparatus.

8. An image processing apparatus comprising:

an extracting unit configured to extract a retinal nerve fiber layer in a plurality of retardation images of an eye;

a detecting unit configured to detect motion of the eye using the extracted retinal nerve fiber layer; and a positioning unit configured to position a plurality of tomographic luminance images corresponding to the plurality of retardation images, using the detected movement.

9. The image processing apparatus according to claim 8, further comprising:

an overlaying unit configured to overlay a plurality of tomographic luminance images which have been positioned; and a display control unit configured to display the overlaid images on a display unit.

10. The image processing apparatus according to claim 8, wherein the plurality of retardation images and the plurality of tomographic luminance images are generated using light having different polarizations by splitting a combined light obtained by combining return light from the eye irradiated by the measurement light and reference light corresponding to the measurement light, the light having different polarizations being detected by a detection unit of an ophthalmologic apparatus.

11. An image processing method comprising:

a step to extract a depolarizing region in a plurality of polarization-sensitive tomographic images of an eye;

a step to detect motion of the eye using the extracted depolarizing region; and a step to position a plurality of tomographic luminance images corresponding to the plurality of polarization-sensitive tomographic images, using the detected movement.

12. The image processing method according to claim 11, wherein the plurality of polarization-sensitive tomographic images are a plurality of DOPU images; and wherein the retinal pigment epithelium is extracted in the plurality of DOPU images as the depolarizing region, in the step to extract.

13. The image processing method according to claim 11, further comprising:

a step to overlay a plurality of tomographic luminance images which have been positioned; and a step to display the overlaid images on a display unit.

14. The image processing method according to claim 11, wherein, in the step to detect, at least one of movement, enlarging/reduction, and rotation, is detected in the plurality of polarization-sensitive tomographic images, as the motion.

15. The image processing method according to claim 11, wherein the plurality of polarization-sensitive tomographic images and the plurality of tomographic luminance images are generated using light having different polarizations, by splitting a combined light obtained by combining return light from the eye irradiated by the measurement light and reference light corresponding to the measurement light.

16. A non-transitory computer-readable storage medium storing a program for causing a computer to execute the steps of the image processing method according to claim 11.

17. An image processing method comprising:

a step to extract a retinal nerve fiber layer in a plurality of retardation images of an eye;

a step to detect motion of the eye using the extracted retinal nerve fiber layer; and a step to position a plurality of tomographic luminance images corresponding to the plurality of retardation images, using the detected movement.

18. A non-transitory computer-readable storage medium storing a program for causing a computer to execute the steps of the image processing method according to claim 17.

19. The image processing method according to claim 17, further comprising:

a step to overlay a plurality of tomographic luminance images which have been positioned; and a step to display the overlaid images on a display unit.

* * * * *